United States Patent

Hüsler et al.

[11] Patent Number: 5,977,357
[45] Date of Patent: Nov. 2, 1999

[54] PHENYL ALKYL KETONE SUBSTITUTED BY CYCLIC AMINE AND A PROCESS FOR THE PREPARATION THEREOF

[75] Inventors: Rinaldo Hüsler, Wünnewil; Rudolf Schwabe, Worb; Reto Luisoli, Höstein, all of Switzerland

[73] Assignee: Ciba Specialty Chemical Corporation, Tarrytown, N.Y.

[21] Appl. No.: 09/088,218

[22] Filed: Jun. 1, 1998

[30] Foreign Application Priority Data

May 3, 1996 [CH] Switzerland ............... 1138/96

[51] Int. Cl.⁶ ............... C07D 207/04; C07D 295/112; C07D 211/32; C07D 233/04
[52] U.S. Cl. ............... 540/611; 544/392; 544/395; 546/194; 546/237; 548/577; 548/950; 548/379.1; 548/347.1
[58] Field of Search .................. 546/194, 237; 544/392, 395; 540/611; 548/577, 950

[56] References Cited

U.S. PATENT DOCUMENTS

| | | | |
|---|---|---|---|
| 1,946,058 | 2/1934 | Britton et al. | 260/64 |
| 2,205,728 | 6/1940 | Martin et al. | 260/457 |
| 3,317,538 | 5/1967 | Freed et al. | 260/268 |
| 4,960,746 | 10/1990 | Husler et al. | 502/153 |
| 4,992,547 | 2/1991 | Berner et al. | 544/162 |
| 5,077,402 | 12/1991 | Desobry et al. | 544/87 |

FOREIGN PATENT DOCUMENTS

| | | |
|---|---|---|
| 0138754 | 5/1988 | European Pat. Off. |
| 0378207 | 7/1990 | European Pat. Off. |
| 0401715 | 12/1990 | European Pat. Off. |
| 0284561 | 5/1993 | European Pat. Off. |
| 200365 | 12/1983 | Switzerland. |
| 1164608 | 9/1969 | United Kingdom. |

OTHER PUBLICATIONS

Carl R. Noller, Chemistry of Organic Compounds, 3rd Ed., W.B. Saunders Company, Philadelphia, PA, p. 259, 1965.
Bull. Chem. Soc. Jpn., 64, 42–49 (1991).
J. Org. Chem. 31 (7), (1966), pp. 2319–2321.
Chem. Berichte 90, 2161, 2174, (1957).
Acta. Chem. Scand. B38, No. 8, pp. 717–719, (1984).
Derwent Abst. 85084B /47 (1979).
Chem. Abst. 92(19): 163712X (1978).
Chemical Abstracts, vol. 108, No. 10, 85724K (1988).
Chem. Pharm. Bull. vol. 41, No. 3, pp. 529–538 (1993).

*Primary Examiner*—Johann Richter
*Assistant Examiner*—Jane C. Osowecki
*Attorney, Agent, or Firm*—Jacob M. Levine; Luther A. R. Hall

[57] ABSTRACT

A novel process for the preparation of compounds of formula I

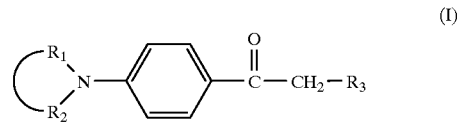

by aminolysis of a p-halophenyl alkyl ketone of formula II

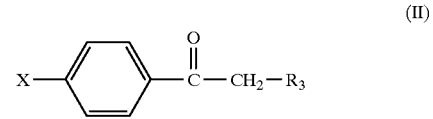

with a cyclic amine of formula III

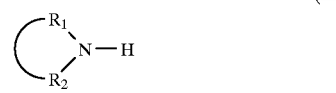

in water at a temperature of at least 130° C., in which formulae X is a halogen atom and $R_1$, $R_2$ and $R_3$ are as claimed in claim 1, as well as the novel compounds of formula I and their use for the preparation of photoinitiators for the photopolymerisation of ethylenically unsaturated compounds.

15 Claims, No Drawings

PHENYL ALKYL KETONE SUBSTITUTED BY CYCLIC AMINE AND A PROCESS FOR THE PREPARATION THEREOF

The present invention relates to novel phenyl alkyl ketones which are substituted by cyclic amine, to a novel process for the preparation thereof, to their use for the preparation of photoinitiators for the photopolymerisation of ethylenically unsaturated compounds, as well as to a photopolymerisable composition comprising such photoinitiators.

EP-B-0284 561 discloses α-aminoacetophenones which are used as photoinitiators. These compounds are prepared by a series of process steps which, in the case of aromatic amines, always start from a derivative of a p-fluorophenylalkylen-1-one, the fluoro in p-position being replaced with an amino group in the final step of the synthesis. This replacement is carried out in an organic solvent, such as dimethylformamide or dimethylsulfoxide, in the presence of potassium carbonate.

One aim of the invention was, inter alia, to develop, on the one hand, reactions which avoid the use of fluoroaromates because these are ecologically problematical, require undesirable waste disposal and because, owing to their relatively high reactivity, they are susceptible to amines and, on the other hand, to get away from organic solvents because working in those results in more or less dark-coloured products with by-products, i.e. in less pure products and lower yields.

The processes known from the literature wherein, in a phenyl alkyl ketone containing halogen in p-position, the halogen in the phenyl nucleus, in particular fluoro or chloro, is replaced with an amine radical, are carried out:

a) in an organic solvent (e.g. EP-B-0138754, reaction of 1-(4-fluorophenyl)-2-methylpropan-1-one with piperidine in dimethylsulfoxide; CH 200 365, reaction of p-chlorostearophenone with dimethylamine in ethanol in the presence of copper powder as catalyst; T. Ibata, Y. isogami, J. Toyoda, Bull. Chem. Soc. Jpn. 64(1) 42–49 (1991), reaction of chloroacetophenone with pyrrolidine in tetrahydrofuran using extremely high pressures (7,2 kbar); J. Org. Chem. 31(7), 2319–21 (1966), reaction of 1-(4-fluorophenyl)propan-1-one with alicyclic amines, such as piperidine, in dimethylformamide or dimethylsulfoxide, or b) without solvents (e.g. B. G. Kresze and H. Goetz, Chern. Berichte 90, 2161, 2174 (1957)), reaction of p-bromoacetophenone with piperidine under reflux with 19% yields of 1-(4-piperidinophenyl)ethanone; or c) in water (e.g.: T. Lundstedt, P. Thoren, R. Carlson, Acta Chemica Scand. B 38, 1984 No. 8 S. 717–719; reaction of p-chloroacetophenone with dimethylamine under pressure in water; U.S. Pat. No. 1,946,058, reaction of p-chloroacetophenone with aqueous ammonia in water under pressure in the presence of copper oxide as catalyst; JP 78-40404, reaction of p-chloroacetophenone with mono- or dialkylamines in water under pressure and in the presence of copper powder as catalyst) where, on the one hand, explosions occurred and, on the other hand, the yields are less than 80%.

Surprisingly, it has now been found that under specific conditions a reaction of p-halophenyl alkyl ketones, in particular of the corresponding p-bromo compounds and p-chloro compounds with amines, especially cyclic amines, in water proceeds very selectively and well, giving high yields.

Only few of such phenyl alkyl ketones, which are substituted in p-position in the phenyl nucleus by a cyclic amine and which additionally have a free methylene group in α-position to the keto group, are known; reference is made to, inter alia, EP-B-0 138 754 (2-methyl-1(4-piperidinophenyl)propan-1-one); CH 200365 (p-dimethylaminostearophone, where the dimethylamino radical according to the description may also be replaced with piperidine without, however, any concrete example being given); G. Kresze and H. Goetz, Chem. Berichte 90, 2161, 2174 (1957), (1-(4-piperidinophenyl)ethanone); T. Ibata, Y. Isogami, J. Toyoda, Bull. Chem. Soc. JPn. 64(1), 42–49 (1991), (1-(4-pyrrolidone)aceto-phenone); and J. Org. Chem. 31(7), 2319–21 (1966), (1-(4-piperidinophenyl)propan-1-one).

The invention, and at the same time the solution to the given problem, relates to novel phenyl alkyl ketones substituted by cyclic amine in p-position, which may be used, inter alia, as novel intermediates for the preparation of specific photoinitiators, as well as to a novel process for the preparation of these intermediates.

The novel phenyl alkyl ketones p-substituted by cyclic amine are compounds of formula (I)

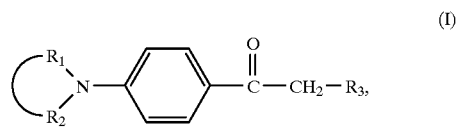

wherein:
R$_1$ and R$_2$ together are straight-chain or branched, unsubstituted or substituted C$_3$–C$_{20}$-alkylene which may be interrupted by one or more than one —O—, —S— or —N(R$_4$) group,
R$_3$ is straight-chain or branched, unsubstituted or substituted C$_2$–C$_{20}$ alkyl, and
R4 is hydrogen, straight-chain or branched C$_1$–C$_3$alkyl, straight-chain or branched C$_3$–C$_5$-alkenyl, C$_7$–C$_9$-phenylalkyl, C$_1$–C$_4$-hydroxyalkyl or phenyl where, if R, and R$_2$ together are unsubstituted tetramethylene, R$_3$ is unsubstituted C$_6$alkyl.

If R$_1$ and R$_2$ together are a C$_3$–C$_{20}$alkylene radical, said radical is, owing to the linking N-atom, a heterocyclic ring system. This N-heterocyclic ring system may be interrupted by one or more than one additional hetero atom, such as an —O—, —S— and/or —N(R$_4$) group, and it can additionally be substituted once or several times.

Suitable C$_3$–C$_{20}$alkylene radicals are straight-chain as well as branched alkylene radicals, and substituents may be e.g. hydroxy, C$_1$–C$_4$alkoxy, hydroxymethyl, C$_1$–C$_4$alkoxymethyl, —COO(C$_1$–C$_4$alkyl) or also phenyl.

Straight-chain or branched C$_3$–C$_{20}$ alkylene radicals are typically tri-, tetra-, penta-, hexa-, hepta-, octa-, deca-, dodeca- or octadecamethylene, and 2,2-dimethyltrimethylene or 1,3,3-trimethyltetramethylene.

C$_3$–C$_{20}$Alkylene which is interrupted by oxygen, sulfur or —N(R$_4$)— can be interrupted once or several times and is typically:
-CH$_2$-CH$_2$-O-CH$_2$-CH$_2$-, -CH$_2$-CH(CH$_3$)-O-CH(CH$_3$)-CH$_2$-,
-CH$_2$-CH$_2$-(O-CH$_2$-CH$_2$-)$_2$-O-CH$_2$-CH$_2$-, -CH$_2$-CH$_2$-(O-CH$_2$-CH$_2$-)$_3$-O-CH$_2$-CH$_2$-,
-CH$_2$-CH$_2$-(O-CH$_2$-CH$_2$-)$_4$-O-CH$_2$-CH$_2$-, -CH$_2$-CH$_2$-O-CH$_2$-CH$_2$-NH-CH$_2$-CH$_2$-O-CH$_2$-CH$_2$-,
-CH$_2$-CH$_2$-(O-CH$_2$-CH$_2$-)$_2$-NH-CH$_2$-CH$_2$-O-CH$_2$-CH$_2$-, -CH$_2$-CH$_2$-(O-CH$_2$-CH$_2$-)$_2$-NH-(CH$_2$-CH$_2$-O-)$_2$-CH$_2$-CH$_2$-,
-CH$_2$-CH$_2$-S-CH$_2$-CH$_2$-,
—CH$_2$—CH$_2$—NH—CH$_2$—CH$_2$—, —CH$_2$—CH$_2$—N(CH$_3$)—CH$_2$—CH$_2$—, —CH(CH$_3$)—CH$_2$—NH—CH(CH$_3$)—CH$_2$—,
—CH$_2$—CH$_2$—NH—CH$_2$—CH$_2$—NH—CH$_2$—CH$_2$—,
—CH$_2$—CH$_2$—CH$_2$—NH—CH$_2$—CH$_2$—CH$_2$—NH—CH$_2$—CH$_2$—CH$_2$—,
—CH$_2$—CH$_2$—(NH—CH$_2$—CH$_2$—)$_2$—NH—CH$_2$—CH$_2$—, —CH$_2$—CH$_2$—(NH—CH$_2$—CH$_2$—)$_4$—NH—CH$_2$—CH$_2$—,
—CH$_2$—CH$_2$—NH—CH$_2$—CH$_2$—CH$_2$—NH—CH$_2$—CH$_2$—NH—CH$_2$—CH$_2$—CH$_2$— or
—CH$_2$—CH$_2$—CH$_2$—NH—CH$_2$—CH$_2$—CH$_2$—NH—CH$_2$—CH$_2$—NH—CH$_2$—CH$_2$—CH$_2$—.

R$_1$ and R$_2$, together with the linking N-atom, are typically the following heterocyclic radicals:

[Structures of heterocyclic radicals: morpholino, dimethylmorpholino, piperazinyl, N-methylpiperazinyl, 2,5-dimethylpiperazinyl, thiomorpholino, piperidinyl, methylpiperidinyl, pyrrolidinyl, azepanyl]

A 6-ring system heterocyclic radical may not be substituted in 6-position

[6-membered ring structure with positions 2,3,4,5,6 labeled]

A 6-ring system is preferred, in particular morpholino.

R$_3$ defined as unsubstituted or substituted C$_2$–C$_{20}$alkyl radical may also be straight-chain or branched. Illustrative examples thereof are the following alkyl radicals: ethyl, propyl, n-butyl, pentyl, hexyl, heptyl, octyl, nonyl, decyl, undecyl, dodecyl, tridecyl, tetradecyl, pentadecyl, hexadecyl, heptadecyl, octadecyl, isopropyl, sec-butyl, isobutyl, tert-butyl, 2-ethylbutyl, isopentyl, 1-methylpentyl, 1,3-dimethylbutyl, 1-methylhexyl, isoheptyl, 1,1,3,3-tetramethylbutyl, 2,2,4,4-tetramethylbutyl, 1-methylheptyl, 3-methylheptyl, 2-ethylhexyl, 1,1,3-trimethylhexyl, 1,1,3,3-tetramethylpentyl, isodecyl, 1-methylundecyl or 1,1,3,3,5,5-hexamethylhexyl.

These C$_2$–C$_{20}$alkyl radicals may additionally be substituted once or several times, e.g. by cyclohexyl, phenyl, C$_1$–C$_4$alkoxy or phenoxy.

In this case, the R$_3$ radicals are typically: 2-methoxyethyl, 3-butoxypropyl, 2-isopropoxyethyl, 4-phenoxybutyl, 2-phenylethyl or 3-phenylpropyl.

Particularly preferred alkyl radicals R3 are unsubstituted, straight-chain or branched alkyl radicals having 2 to 10 carbon atoms, preferably those having 2 to 7 carbon atoms, particularly preferably those having 2 to 5 carbon atoms, such as ethyl or propyl.

R$_4$ defined as C$_1$–C$_3$alkyl may be straight-chain or branched and is typically methyl, ethyl, n- and isopropyl.

R$_4$ defined as C$_3$–C$_5$alkenyl is straight-chain or branched alkenyl, typically propenyl or allyl, butenyl, such as 2-butenyl, 3-butenyl and isobutenyl, and pentenyl, such as n-2,4-pentadienyl.

R$_4$ defined as C$_7$–C$_9$phenylalkyl is typically benzyl, α-methylbenzyl, α,α-dimethylbenzyl or 2-phenylethyl.

R$_4$ defined as C$_1$–C$_4$hydroxyalkyl is typically 2-hydroxyethyl, 2-hydroxypropyl or 2-hydroxy-isobutyl.

In the preferred compounds of formula I, R$_4$ is hydrogen, C$_1$–C$_3$alkyl, allyl, benzyl or C$_2$–C$_3$-hydroxyalkyl and, preferably, hydrogen or methyl.

Preferred compounds are those conforming to formula I, wherein:

R$_1$ and R$_2$ together are C$_3$–C$_{20}$alkylene which is unsubstituted or substituted by hydroxy, C$_1$–C$_4$alkoxy, hydroxymethyl, C$_1$–C$_4$alkoxymethyl, —COO(C$_1$–C$_4$alkyl) or phenyl and which may be interrupted by one or more than one —O—, —S— or —N(R$_4$) group, R$_3$ is C$_2$–C$_{20}$alkyl which is unsubstituted or substituted by C$_1$–C$_4$alkoxy, phenoxy, cyclohexyl or phenyl, and R$_4$ is hydrogen, C$_1$–C$_3$alkyl, C$_3$–C$_5$alkenyl, C$_7$–C$_9$phenylalkyl, C$_1$–C$_4$hydroxyalkyl or phenyl, in particular those compounds, wherein:

R$_1$ and R$_2$ together are straight-chain or branched C$_4$–C$_{12}$alkylene which may be interrupted by an —O—, —S— or —N(R$_4$) group, R$_3$ is C$_2$–C$_{10}$alkyl, and R$_4$ is hydrogen, C$_1$–C$_3$alkyl, allyl, benzyl or C$_2$–C$_3$hydroxyalkyl, or wherein:

R$_1$ and R$_2$ together are straight-chain or branched C$_4$–C$_8$alkylene forming a 6-membered ring which may be interrupted by an —O—, —S— or —N(R$_4$) group, R$_3$ is C$_2$–C$_7$alkyl, and R$_4$ is hydrogen or methyl, and preferably those, wherein:

R$_1$ and R$_2$, together with the linking N-atom, are a 6-membered ring which may additionally be interrupted by an —O—, —S— or —N(R$_4$) group, or wherein:

R$_1$ and R$_2$, together with the linking N-atom, are a morpholinyl, dimethylmorpholinyl, piperazinyl, N-methylpiperazinyl or 2,5-dimethylpiperazinyl radical, and in particular those, wherein R$_1$ and R$_2$, together with the linking N-atom, form the morpholinyl radical.

The preparation of the compounds of formula I is carried out by a novel process constituting another aspect to which this invention relates.

This novel process for the preparation of compounds of formula I

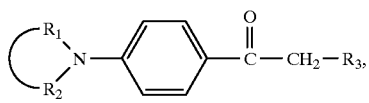

(I)

wherein:
R₁ and R₂ together are straight-chain or branched, unsubstituted or substituted $C_3$–$C_{20}$alkylene which may be interrupted by one or more than one —O—, —S— or —N(R₄) group,
R₃ is straight-chain or branched, unsubstituted or substituted $C_2$–$C_{20}$ alkyl, and
R₄ is hydrogen, straight-chain or branched $C_1$–$C_3$alkyl, straight-chain or branched $C_3$–$C_5$alkenyl, $C_7$–$C_9$phenylalkyl, $C_1$–$C_4$hydroxyalkyl or phenyl, consists in the aminolysis of a p-halophenyl alkyl ketone of formula II

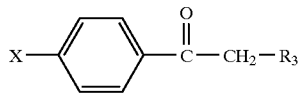

(II)

with a cyclic amine of formula III

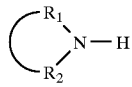

(III)

in water at a temperature of at least 130° C., in which formulae X is a halogen atom and R₁, R₂ and R₃ are as defined for formula I.

The p-halophenyl alkyl ketone of formula II is preferably one wherein X is bromo and, preferably, chloro.

The cyclic amine of formula III is preferably present in excess amount, based on the p-halophenyl alkyl ketone of formula II. This excess is preferably from about 2.5 to 20, more preferably from 2.5 to 12, molar equivalents.

The water is present in an amount from about 1 to 100, preferably from 2 to 20 and, more preferably, from 2.5 to 10, molar equivalents, based on 1 molar equivalent of the p-halophenyl alkyl ketone of formula II; however, larger amounts of water are not critical either.

The reaction is conveniently carried out under pressure (c. 3–30 bar) in a pressure vessel, preferably in a steel high-pressure reactor equipped with blade agitator, manometer and thermocouple. However, it is also possible to carry out the reaction without pressure vessel under reflux (c. 105° C.–110° C.).

The temperature is conveniently in the range from about 140° C. to 240° C., preferably from 150° C. to 230° C. When working with the p-bromophenyl alkyl ketone of formula II, the temperature is in the range from about 140° C. to 200° C., preferably from 160° C. to 180° C., and when working with the p-chlorophenyl alkyl ketone of formula II, the temperature is in the range from about 180° C. to 240° C., preferably from 200° C. to 230° C.

Catalysts may, but do not have to, be added. Altough they accelerate the reaction to a certain extent, working without catalysts reduces the ecological problems and renders the advantages of adding heavy metals less important.

Suitable catalysts are in particular:
copper compounds or nickel compounds or the salts thereof, typically copper(I) chloride, copper(I) bromide, copper(I) iodide, copper(II) bromide, copper (II) chloride, copper carbonate, copper(II) sulfate, copper oxide as well as copper powder, or nickel acetate, nickel oxide, nickel chloride and nickel bromide.

These catalysts are used in amounts from about 0.1 to 15% by weight, preferably from 0.5 to 5% by weight, based on 100.0% by weight of p-halophenyl alkyl ketone of formula II.

Further solvents are, in principle, not required for carrying out the reaction, but may additionally be used. Convenient solvents have been found to be high boiling and polar solvents, typically diethylene glycol, diethylene glycol monomethyl ether, diethylene glydol dimethyl ether, benzyl alcohol, phenylethyl alcohol or phenoxyethanol.

The reaction of the cyclic amine of formula III with the p-halophenyl alkyl ketone of formula II is preferably carried out such that, either:
a) the p-halophenyl alkyl ketone of formula II is placed, together with the water and the cyclic amine, in the reaction vessel and is immediately heated to the final temperature, or
b) the p-halophenyl alkyl ketone of formula II, together with the water and the amine, is placed in the reaction vessel and heated slowly over hours during the reaction to the final temperature, or
c) the p-halophenyl alkyl ketone of formula II is added during the reaction, preferably in fused form, to the water and the cyclic amine which have been previously heated to the reaction temperature. This process variant reduces or eliminates in particular the risk of an autocatalytic degradation at very high temperatures. The process can be carried out, for example, by placing all components in a reaction vessel and adding the p-bromophenyl alkyl ketone of formula II in the temperature range from about 140° C.–190° C. over hours, the temperature being slowly raised over about 3–12 hours from the lower to the higher temperature level, or by adding the p-chlorophenyl alkyl ketone of formula II in the temperature range from about 180° C.–230° C. over hours, the temperature being slowly raised over about 3–12 hours from the lower to the higher temperature level.

For safety reasons the accumulation of the p-halophenyl alkyl ketone is expediently kept under control.

A preferred process method is typically that, which comprises placing 1 part (here and hereinbelow, parts are based on mol amounts) of p-bromophenyl alkyl ketone or 1 part of p-chlorophenyl alkyl ketone of formula II, wherein R₃ is straight-chain or branched, unsubstituted $C_2$–$C_7$alkyl, with 5 parts of a cyclic amine of formula III, wherein R₁ and R₂ together are $C_4$–$C_6$alkylene which may be interrupted by an —O—, —S— or —N(R₄) group and R₄ is hydrogen or methyl, and with 5 parts of water in a reaction vessel and reacting this mixture at a temperature from about 160° C.–180° C. or 200° C.–230° C., or that method, which comprises placing 10 to 20 parts of a cyclic amine of formula III, wherein R₁ and R₂ together are $C_4$–$C_6$alkylene which may be interrupted by an —O—, —S— or —N(R₄) group and R₄ is hydrogen or methyl, with 20 to 40 parts of water in a reaction vessel, adding 2 to 4 parts of p-chlorophenyl alkyl ketone of formula II, wherein R₃ is straight-chain or branched, unsubstituted $C_2$–$C_7$alkyl, and reacting this mixture under pressure at about 210° C.–230° C.

The processing and purification of the novel phenyl alkyl ketones of formula I, which are substituted by a cyclic amine, is carried out by known methods, typically by distillation, crystallisation and filtration.

The cyclic amines of formula III are known, some being commercially available, and can be prepared in known manner (e.g. Houben-Weyl, Vol. 11/1 (1957) p. 26–29, 32–33 and 63–67; Org. Synth. Coll. Vol. 3, 307 (1955); JACS 109, 1496–1502 (1987) or Tetrahedron Vol. 40, 1433–1456 (1984).

Said cyclic amines are typically the following compounds: morpholine, piperidine, pyrrolidine, piperazine, N-methylpiperazine, 2,6-dimethylmorpholine, dimethylpiperidine, dimethylpiperazine, thiomorpholine, 4-hydroxypiperidine, 3-ethoxycarbonylpiperidine or hexamethylene mine.

The p-halophenyl alkyl ketones of formula II are also known (e.g. Friedel-Crafts and related Reactions, Ed. C. A. Olah, J. Wiley and Sons, N.Y. (1964) Vol. 3, Parts 1+2; Chem. Rev. 55, 229 (1955); Org. Synth. Coll. Vol. 3, 14 (1955) and JACS 109,7122 (1987).

Illustrative examples of single compounds are: 1-(4-bromophenyl)-n-butan-1-one, 1-(4-bromophenyl)-n-pentan-1-one, 1-(4-bromophenyl)-n-hexan-1-one, 1-(4-bromophenyl)-n-heptan-1-one, 1-(4-bromophenyl)--n-octan-1-one, 1-(4-bromophenyl)-isononan-1-one, 1-(4-chlorophenyl)-n-butan-1-one and 1-(4-chlorophenyl)-n-pentan-1-one.

The preparation of the p-halophenyl alkyl ketones of formula II is carried out in known manner, typically by a Friedel-Crafts reaction from a halobenzene and an alkanecarboxylic acid chloride in accordance with the following reaction scheme:

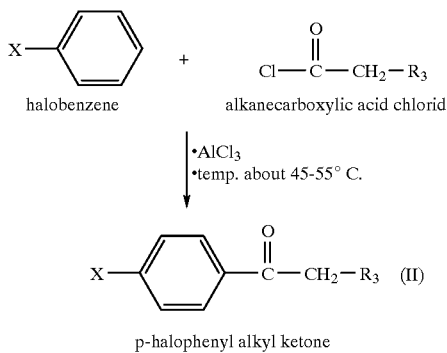

X in these formulae is a halogen atom, preferably chloro or bromo, and $R_3$ has the meaning cited above.

Both educts, the halobenzene and the alkanecarboxylic acid chloride, are known.

Typical examples of halobenzenes are, preferably, monobromobenzene and, in particular, monochlorobenzene.

Typical examples of alkanecarboxylic acid chlorides are e.g. butyric acid chloride, isobutyric acid chloride, n-valeric acid chloride, isovaleric acid chloride, hexanoic acid chloride, enanthic acid chloride, caprylic acid chloride, pelargonic acid chloride, capric acid chloride, lauric acid chloride, myristic acid chloride, palmitic acid chloride, stearic acid chloride, arachinic acid chloride, eicosancarboxylic acid chloride and behenic acid chloride.

The p-halophenyl alkyl ketone of formula II obtained by this reaction must be isolated prior to being further reacted with the cyclic amine of formula III.

It is surprising, and was not to be foreseen on the basis of the literature mentioned at the outset, that the addition of water to the reaction of the p-halophenyl alkyl ketone of formula II with the cyclic amine of formula III very efficiently prevents the formation of coloured by-products and resinifications, giving very pure bright products having a purity of >99.0%.

Compared to processing in organic solvents, such as dimethylsulfoxide or dimethylformamide, processing in water is ecologically advantageous, especially in large scale production.

It is also surprising that the reaction of the p-halophenyl alkyl ketone of formula II with the cyclic amine of formula III, i.e. the halogen replacement in the case of a little-activated benzene derivative, proceeds so smoothly and quickly in water.

It is also surprising that the aminolysis reaction proceeds without the compulsory addition of a catalyst and gives high yields of 88% to 96%; the absence of a catalyst furthermore saves having to remove it from the final product which usually involves a time-consuming process.

The use of compounds of formula I

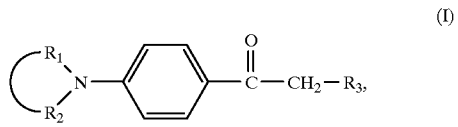

wherein:

$R_1$ and $R_2$ together are straight-chain or branched, unsubstituted or substituted $C_3$–$C_{20}$-alkylene which may be interrupted by one or more than one —O—, —S— or —N($R_4$) group, $R_3$ is straight-chain or branched, unsubstituted or substituted $C_2$–$C_{20}$alkyl, and $R_4$ is hydrogen, straight-chain or branched $C_1$–$C_3$alkyl, straight-chain or branched $C_3$–$C_5$-alkenyl, $C_7$–$C_9$phenylalkyl, $C_1$–$C_4$hydroxyalkyl or phenyl, or of the compounds obtained by the stated novel process, in particular for preparing radical photoinitiators of formula IV

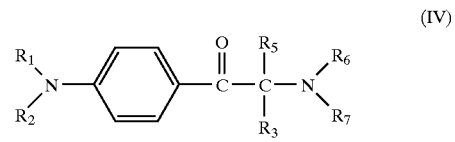

or their acid addition salts, wherein:

$R_1$ and $R_2$ together are straight-chain or branched, unsubstituted $C_3$–$C_{20}$alkylene which may be interrupted by one or more than one —O—, —S— or —N($R_4$) group and/or which may be substituted by hydroxy, $C_1$–$C_4$alkoxy, hydroxymethyl, $C_1$–$C_4$alkoxymethyl, —COO($C_1$–$C_4$alkyl) or phenyl;

$R_3$ is straight-chain or branched $C_2$–$C_{20}$alkyl which is unsubstituted or substituted by $C_1$–$C_4$alkoxy, phenoxy, cyclohexyl or phenyl, $R_4$ is hydrogen, $C_1$–$C_3$alkyl, $C_3$–$C_5$alkenyl, $C_7$–$C_9$phenylalkyl, $C_1$–$C_4$hydroxyalkyl or pheryl;

$R_5$ is either (a) a radical of formula

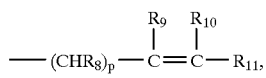

wherein p is 0 or 1,
or (b) a radical of formula

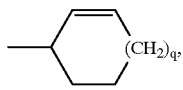

wherein q is 0, 1, 2 or 3,
or (c) a radical of formula

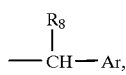

wherein Ar is a phenyl, naphthyl, furyl, thienyl or pyridyl radical which is unsubstituted or substituted by halogen, OH, $C_1$–$C_{12}$alkyl, or by $C_1$–$C_4$alkyl which is substituted by OH, halogen, —N($R_{12}$)$_2$, $C_1$–$C_{12}$alkoxy, —COO ($C_1$–$C_{18}$alkyl), —CO(OCH$_2$CH$_2$)$_n$OCH$_3$ or —OCO ($C_1$–$C_4$)-alkyl; by $C_1$–$C_{12}$-alkoxy, or by $C_1$–$C_4$alkoxy which is substituted by —COO($C_1$–$C_{18}$alkyl) or —CO (OCH$_2$CH$_2$)$_n$ OCH$_3$; or by —(OCH$_2$CH$_2$)$_n$OH, —(OCH$_2$CH$_2$)$_n$OCH$_3$, $C_1$–$C_8$alkylthio, phenoxy, —COO ($C_1$–$C_{18}$alkyl), —CO(OCH$_2$CH$_2$)$_n$OCH$_3$, phenyl or benzoyl, wherein n is 1–20, in which formulae $R_{12}$ is hydrogen, $C_1$–$C_8$alkyl, $C_3$–$C_5$alkenyl, $C_7$–$C_9$phenylalkyl, $C_1$–$C_4$hydroxyalkyl or phenyl, $R_8$ is hydrogen, $C_1$–$C_8$alkyl or phenyl, and $R_9$, $R_{10}$ and $R_{11}$ are each independently of one another hydrogen or $C_1$–$C_4$alkyl, or $R_9$ and $R_{10}$ taken together are $C_3$–$C_7$alkylene, $R_6$ is hydrogen, $C_1$–$C_{12}$alkyl; $C_2$–$C_4$alkyl which is substituted by hydroxy, $C_1$–$C_4$alkoxy, —CN or —COO ($C_1$–$C_4$alkyl); $C_3$–$C_5$alkenyl, $C_5$–$C_{12}$cycloalkyl or $C_7$–$C_9$phenylalkyl, $R_7$ is $C_1$–$C_{12}$alkyl; $C_2$–$C_4$alkyl which is substituted by hydroxy, $C_1$–$C_4$alkoxy, —CN or —COO($C_1$–$C_4$alkyl); $C_3$–$C_5$alkenyl, $C_5$–$C_{12}$cycloalkyl, $C_7$–$C_9$phenylalkyl, phenyl, or phenyl which is substitued by halogen, $C_1$–$C_{12}$alkyl, $C_1$–$C_4$alkoxy or —COO($C_1$–$C_4$alkyl), or $R_7$, together with $R_3$, is $C_1$–$C_7$alkylene, $C_7$–$C_{10}$phenylalkylene, o-xylylene, 2-butenylene or $C_2$–$C_3$oxaalkylene or azaalkylene, or $R_6$ and $R_7$ together are $C_3$–$C_7$alkylene which may be interrupted by —O—, —S—, —CO—or —N($R_{13}$)— or which may be substituted by hydroxy, $C_1$–$C_4$alkoxy or —COO($C_1$–$C_4$alkyl), wherein $R_{13}$ is hydrogen, $C_1$–$C_{12}$alkyl which may be interrupted by one or more than one —O—; $C_3$–$C_5$alkenyl, $C_7$–$C_9$phenylalkyl, $C_1$–$C_4$hydroxyalkyl, —CH$_2$CH$_2$CN, —CH$_2$CH$_2$COO ($C_1$–$C_4$alkyl), $C_2$–$C_8$alkanoyl or benzoyl.

The process of this invention thus permits in a simple manner, which may be very well realised in large scale production, the preparation of photoinitiators of formula IV starting from monohalobenzene and an acid chloride of formula

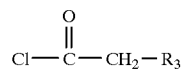

by a Friedel Crafts reaction to a p-halophenyl alkyl ketone of formula II and the aminolysis thereof,
with a cyclic amine of formula III

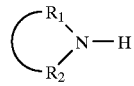 (III)

in water at a temperature of at least 130° C., in which formulae X is a halogen atom and $R_1$, $R_2$ and $R_3$ are as defined above, to a cyclic amine-substituted phenyl alkyl ketone of formula I

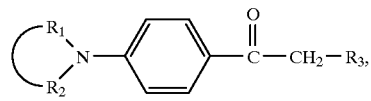 (I)

halogenation of this phenyl alkyl ketone compound of formula I, reaction with an amine of formula

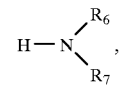

subsequent reaction with a compound introducing $R_5$, and Stevens rearrangement under basic conditions.

The halogenation of the phenyl alkyl ketone compound of formula I is an α-halogenation with e.g. bromo or chloro in a solvent, such as glacial acetic acid, at room temperature. The subsequent amination with an amine of formula

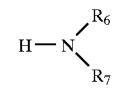

wherein $R_6$ and $R_7$ are as defined above (e.g. dimethylamine) is carried out in a suitable solvent e.g. methyl ethyl ketone. After the amination, the reaction is carried out with a compound introducing the $R_5$ group, typically benzyl bromide, benzyl chloride, allyl bromide or allyl chloride with subsequent Stevens rearrangement under basic conditions, e.g. NaOH or KOH.

Owing to the presence of a basic amino group, the photoinitiators of formula IV may be converted into the corresponding acid addition salts by the addition of acids. These acids can be inorganic or organic acids. Illustrative examples of such acids are HCl, HBr, $H_2SO_4$, $H_3PO_4$, mono- or polycarboxylic acids, typically acetic acid, oleic acid, succinic acid, sebacic acid, tartaric acid or $CF_3COOH$, sulfonic acids such as $CH_3SO_3H$, $C_{12}H_{25}SO3H$, p-$C_{12}H_{25}C6H_4$—$SO_3H$, p-$CH_3$–$C_6H_4$—$SO_3H$ or $CF_3SO_3H$, acrylic acid, methacrylic acid, polyacrylic acid, polymethacrylic acid and benzoic acid.

Photoinitiators for radical polymerisable compounds are those compounds which break down into radical fragments when irradiated with shortwave light and which are the actual initiators for the polymerisation of the ethylenically unsaturated compounds.

These photoinitiators are mainly used for the photopolymerisation of ethylenically unsaturated compounds or mixtures comprising such compounds, for photocuring pigmented systems such as printing inks or white finishes, for photocuring non-pigmented systems, such as UV-curable printing inks, for preparing photoresists and printing plates and for exterior varnishes which postcure on the surface in daylight.

The unsaturated compounds can contain one or more than one olefinic double bond and may be low molecular (monomeric) or higher molecular (oligomeric). Illustrative examples of monomers containing a double bond are alkyl acrylates or hydroxyalkyl acrylates, or alkyl methacrylates or hydroxyalkyl methacrylates, typically methyl acrylate, ethyl acrylate, butyl acrylate, 2-ethylhexyl acrylate or 2-hydroxyethyl acrylate, isobornyl acrylate, methyl methacrylate or ethyl methacrylate. Further examples are acrylfnitrile, acryl amide, methacryl amide, N-substituted (meth)acrylamides, vinyl esters such as vinyl acetate, vinyl ethers such as isobutyl vinyl ether, styrene, alkyl styrene, halogen styrene, N-vinyl pyrrolidone, vinyl chloride or vinylidene chloride.

Illustrative examples of monomers containing several double bonds are ethylene glycol diacrylate, propylene glycol diacrylate, neopentyl glycol diacrylate, hexamethylene glycol diacrylate or bisphenol A diacrylate, 4,4'-bis(2-acryloyloxyethoxy)diphenylpropane, trimethylolpropane triacrylate, pentaerythritol triacrylate or pentaerythritol tetraacrylate, vinyl acrylate, divinyl benzene, divinyl succinate, diallyl phthalate, triallyl phosphate, triallyl isocyanurate or tris(2-acryloyloxyethyl)isocyanurate.

Illustrative examples of higher molecular (oligomeric) polyunsaturated compounds are acrylated epoxy resins, acrylated polyethers, acrylated polyurethanes or acrylated polyesters. Other examples of unsaturated oligomers are unsaturated polyester resins, which are mostly prepared from maleic acid, phthalic acid and one or more than one diol and which have a molecular weight from about 500 to 3000. Such unsaturated oligomers can also be called prepolymers.

Often, two-component mixtures of a prepolymer with a polyunsaturated monomer, or three-component mixtures which additionally contain a monounsaturated monomer, are used. The prepolymer is in this case in particular decisive for the properties of the paint film and by varying it, the skilled person can influence the properties of the cured film. The polyunsaturated monomer acts as crosslinker which makes the paint film insoluble. The monounsaturated monomer acts as reactive diluent for lowering the viscosity, rendering the use of a solvent unnecessary.

Such two- and three-component systems based on a prepolymer are used for printing inks as well as for paints, photoresists or other photocurable compounds. The binders used for printing inks are often also one-component systems based on photocurable prepolymers.

Unsaturated polyester resins are mostly used in two-component systems together with a monounsaturated monomer, preferably styrene. For photoresists, specific one-component systems are often used, such as polymaleinimides, polycralcones or polyimides, as described in DE-OS 2 308 830.

The unsaturated compounds can also be used in admixture with non-photopolymerisable film-forming components. Said components can, for example, be physically drying polymers or their solutions in organic solvents, typically nitrocellulose or cellulose acetobutyrate. However, they can also be chemically or thermally curable resins such as polyisocyanates, polyepoxides or melamine resins. The additional use of thermally curable resins is important for use in so-called hybrid systems which are photopolymerised in a first step and then crosslinked by heat aftertreatment in a second step.

In addition to the photoinitiator, the photopolymerisable mixtures can also comprise different additives. Typical examples thereof are thermal inhibitors to prevent a premature polymerisation, such as hydroquinone or sterically hindered phenols. To enhance the dark storage stability it is possible to use e.g. copper compounds, phosphorus compounds, quaternary ammonium compounds or hydroxylamine derivatives. For the purpose of exluding the atmospheric oxygen during polymerisation, it is possible to add paraffin or similar wax-like substances which migrate to the surface at the beginning of the polymerisation. As light stabilisers, small amounts of UV absorbers, such as those of the benzotriazole, benzophenone or oxalanilide type, may be added. Even better is the addition of light stabilisers which do not absorb UV light, typically sterically hindered amines (HALS).

In specific cases it may be advantageous to use mixtures of two or more photoinitiators of formula IV. It is, of course, also possible to use mixtures with known photoinitiators, typically mixtures with benzophenone, acetophenone derivatives, benzoin ethers, benzil ketals, monoacryl phosphine oxides or bisacyl phosphine oxides.

To accelerate the photopolymerisation it is possible to add amines such as triethanol amine, N-methyldiethanol amine, ethyl p-dimethylaminobenzoate, Michler's ketone or bisdiethylaminobenzophenone. The action of the amines can be enforced by adding aromatic ketones of the benzophenone type.

Acceleration of the photopolymerisation can also be achieved by adding photosensitisers which shift or broaden the spectral sensitivity. Such photosensitisers are in particular aromatic carbonyl compounds such as benzophenone derivatives, thioxanthone derivatives, anthraquinone derivatives and 3-acylcoumarine derivatives and also 3-(aroylmethylene)-thiazolines.

The effectivity of the photoinitiators may be enhanced by the addition of titanocene derivatives with fluororganic radicals, such as disclosed in EP-A-122 223, 186 626 and 318 894, typically in an amount of 0.1–20%. Illustrative examples of such titanocenes are bis-(methylcyclopentadienyl)-bis-(2,3,6-trifluorophenyl) titanium, bis(cyclopentadienyl)-bis(4-di-butylamino-2,3,5, 6-tetrafluorophenyl)titanium, bis(methylcyclopentadienyl)-2-(trifluoro-methyl)phenyl titanium isocyanate, bis (cyclopentadienyl)-2-(trifluoromethyl)phenyl titanium trifluoroacetate, bis(methylcyclopentadienyl)-bis(4-decyloxy-2,3,5,6-tetrafluorophenyl)-titanium, bis (cyclopentadienyl)-bis-[2,6-difluoro-3-(pyrr-1-yl)phenyl] titanium, bis(methylcyclopentadienyl)-bis-[2,6-difluoro-3-(pyrr-1-yl)phenyl]titanium, bis(cyclopentadienyl)-bis-[2,6-difluoro-3-(2,5-dimethylpyrr-1-yl)phenyl]titanium and bis (methylcyclopentadienyl)-bis-[2,6-difluoro-3-(2,5-dimethylpyrr-1-yl)phenyl]titanium. Liquid α-aminoketones are particularly suitable for these mixtures.

The photopolymerisable composition, comprising
A) at least one ethylenically unsaturated photopolymerisable compound, and
B) at least one photoinitiator of formula IV and,
C) optionally, further known and customary additives can be used for different purposes. Of particular importance is their use in pigmented or coloured systems, such as printing inks, for photographic reproduction processes, image recording processes and for the preparation of relief forms.

Another important field of application are exterior varnishes which may be pigmented or non-pigmented. Particularly important are the mixtures in white finishes, which are understood to be $TiO_2$-pigmented exterior varnishes. The pigment present in the photocurable compounds may be an inorganic pigment, typically titanium dioxide (rutile or anatase), iron oxide yellow, iron oxide red, chromium yellow, chromium green, nickel titanium yellow, ultramarine blue, cobalt blue, cadmium yellow, cadmium red or zinc white. The pigment may be an organic pigment, typically a monoazo pigment or bisazo pigment, or a metal complex thereof, a phthalocyanine pigment, a polycyclic pigment, typically a perylene, thioindigo, flavanthrone, quinacridone, tetrachlorisoindolinone or triphenylmethane pigment. However, the pigment may also be carbon black or a metal powder, typically aluminium powder or copper powder. The pigment can also be a mixture of two or more different pigments conventionally used to obtained specific shades.

The pigment can be present in an amount from 5 to 60% by weight, based on the total amount. In printing inks, the pigment is usually present in an amount from 10–30%.

Further fields of application are the radiation curing of photoresists, the photocrosslinking of silver-free films as well as the preparation of printing plates. Another use is that for exterior varnishes which postcure on the surface by daylight. In photoresists or reprographic films, dyes are also often used instead of pigments for colouring. These dyes may be organic dyes of a very wide variety of classes, typically azo dyes, methine dyes, anthraquinone dyes or metal complex dyes. In the concentrations used, these dyes are soluble in the respective binders. The customary concentrations are from 0.1 to 20% by weight, preferably from 1–5% by weight, based on the entire composition.

In the cited fields of application, the photoinitiators are conveniently used in amounts from 0.1 to 20% by weight, preferably from about 0.5 to 5% by weight, based on the photopolymerisable composition.

Polymerisation is carried out by the known methods of photopolymerisation by irradiation with light which is rich in shortwave radiation. Suitable lights sources are, for example, medium-pressure mercury lamps, high-pressure mercury lamps and low-pressure mercury lamps, superactinic fluorescent tubes, metalhalide lamps or lasers, the emission maxima of which are in the range from 250 to 450 nm. In the case of a combination with photosensitisers or ferrocene derivatives it is also possible to use long-wave light or laser rays of up to 600 nm.

THE FOLLOWING NON-LIMITATIVE
EXAMPLES ILLUSTRATE THE INVENTION.

EXAMPLE 1

181.7 g (0.80 mol) of 1-(4-bromophenyl)butan-1-one, 348.5 g (4.0 mol) of morpholine purum and 72.0 g (4.0 mol) of deionised water are placed in a 1 l high-pressure reactor. The reactor is closed and the solution is heated to 170° C. over about 90 minutes.

The pressure in the reactor rises from 0 to 5–6 bar and stabilises 1 hour later at 4–5 bar. The reaction solution is stirred for about 28 hours at about 170° C. Subsequently, the reaction solution is cooled and taken out of the reactor at about 80° C.

The reaction solution is heated to about 104° C. in a distillation apparatus to distill off the water. The morpholine is then removed by distillation under a weak vacuum. After the distillation, 144.0 g (0.80 mol) of sodium methylate solution 30% in methanol are added and the suspension is heated to remove the methanol by distillation. When the methanol distillation is complete, the reaction mixture is evacuated and the morpholine is removed by distillation. Subsequently, 90 g of deionised water are added at about 80° C. and stirred. The water is then separated off. The remaining phase (about 196 g of crude yield, c. 105% of theory) is diluted with 150 ml (117.5 g) of isopropanol, cooled and seeded for crystallisation. The suspension is filtered at about −10° C. and washed with cold isopropanol, giving 148.7 g 1-(4-morpholinophenyl)butan-1 -one (79.6% of theory) in the form of pale beige crystals having an m.p. of 64.5° C.–65.5° C. and a purity of >99.0%.

Elemental analysis:

|  | % C |  | % H |  | % N |
|---|---|---|---|---|---|
| calculated: | 72.07 | calculated: | 8.21 | calculated: | 6.00 |
| found: | 72.03 | found: | 8.29 | found: | 5.92 |

It is possible to obtain a further 19.8 g (c. 10% of theory) of 1-(4-morpholinophenyl)butan-1-one from the filtrate (isopropanol).

The procedure of Example 1 is repeated, but using equimolecular amounts of the cyclic amines according to Table 1 and equimolecular amounts of the 1-(4-bromophenyl)alkyl ketone according to Table 1, giving the phenyl alkyl ketone compounds substituted by cyclic amines according to Table 1, the physical analysis data of which are also indicated in Table 1.

TABLE 1

| Ex. | Cyclic amine | 1-(4-bromophenyl)alkyl ketone | Phenyl alkyl ketone substituted by cyclic amine | m.p. °C. | | % C | % H | % N |
|---|---|---|---|---|---|---|---|---|
| 2 | morpholine (N—H, O) | 4-Br-C₆H₄—CO—CH₂—C₃H₇ | 4-(morpholino)-C₆H₄—CO—CH₂—C₃H₇ | 68.5–70.5 | calcd. found | 72.84 72.86 | 8.56 8.76 | 5.66 5.36 |
| 3 | 2,6-dimethylmorpholine | 4-Br-C₆H₄—CO—CH₂—C₂H₅ | 4-(2,6-dimethylmorpholino)-C₆H₄—CO—CH₂—C₂H₅ | 90.2–91.7 | calcd. found | 73.54 73.57 | 8.87 8.85 | 5.36 5.28 |
| 4 | 2,6-dimethylmorpholine | 4-Br-C₆H₄—CO—CH₂—C₃H₇ | 4-(2,6-dimethylmorpholino)-C₆H₄—CO—CH₂—C₃H₇ | 76.7–77.3 | calcd. found | 74.15 74.15 | 9.15 9.18 | 5.09 5.04 |
| 5 | piperazine (N—H / N—H) | 4-Br-C₆H₄—CO—CH₂—C₂H₅ | 4-(piperazinyl)-C₆H₄—CO—CH₂—C₂H₅ | 67–69 | calcd. found | 72.38 72.44 | 8.68 8.51 | 12.06 12.01 |
| 6 | piperazine (N—H / N—H) | 4-Br-C₆H₄—CO—CH₂—C₃H₇ | 4-(piperazinyl)-C₆H₄—CO—CH₂—C₃H₇ | 61–65.2 | calcd. found | 73.13 73.22 | 9.00 9.6 | 11.37 11.35 |
| 7 | 4-methylpiperazine (H₃C—N / N—H) | 4-Br-C₆H₄—CO—CH₂—C₂H₅ | 4-(4-methylpiperazinyl)-C₆H₄—CO—CH₂—C₂H₅ | 96–98 | calcd. found | 73.13 73.17 | 9.00 9.03 | 11.37 11.34 |

TABLE 1-continued

| Ex. | Cyclic amine | 1-(4-bromophenyl)alkyl ketone | Phenyl alkyl ketone substituted by cyclic amine | m.p. °C. | Physical analysis data %C | %H | %N |
|---|---|---|---|---|---|---|---|
| 8 | 4-methylpiperazine (H₃C—N∠N—H) | Br—C₆H₄—CO—CH₂—C₃H₇ | H₃C—N(piperazine)—C₆H₄—CO—CH₂—C₃H₇ | 74.1–76.8 | calcd. 73.81 found 74.04 | 9.29 9.27 | 10.76 10.65 |
| 9 | 2,5-dimethylpiperazine | Br—C₆H₄—CO—CH₂—C₂H₅ | 2,5-dimethylpiperazinyl—C₆H₄—CO—CH₂—C₂H₅ | 74.6–76.7 | calcd. 73.81 found 74.03 | 9.29 9.55 | 10.76 10.76 |
| 10 | thiomorpholine | Br—C₆H₄—CO—CH₂—C₂H₅ | thiomorpholinyl—C₆H₄—CO—CH₂—C₂H₅ | 27–31 | calcd. 67.43 found 67.50 | 7.68 7.85 | 5.62 5.75 |
| 11 | piperidine | Br—C₆H₄—CO—CH₂—C₂H₅ | piperidinyl—C₆H₄—CO—CH₂—C₂H₅ | 47.5–49.5 | calcd. 77.88 found 77.66 | 9.15 9.27 | 6.05 5.95 |
| 12 | piperidine | Br—C₆H₄—CO—CH₂—C₃H₇ | piperidinyl—C₆H₄—CO—CH₂—C₃H₇ | 56.8–60.1 | calcd. 78.32 found 78.33 | 9.45 9.42 | 5.71 5.57 |
| 13 | 3,3-dimethylpiperidine | Br—C₆H₄—CO—CH₂—C₂H₅ | 3,3-dimethylpiperidinyl—C₆H₄—CO—CH₂—C₂H₅ | 47–48.7 | calcd. 78.72 found 78.61 | 9.71 9.90 | 5.40 5.31 |
| 14 | pyrrolidine | Br—C₆H₄—CO—CH₂—C₂H₅ | pyrrolidinyl—C₆H₄—CO—CH₂—C₂H₅ | 83.5–85.3 | calcd. 77.38 found 77.25 | 8.81 8.89 | 6.45 6.40 |

TABLE 1-continued

| Ex. | Cyclic amine | 1-(4-bromophenyl)alkyl ketone | Phenyl alkyl ketone substituted by cyclic amine | m.p. °C | % C | % H | % N |
|---|---|---|---|---|---|---|---|
| 15 | pyrrolidine (N–H) | Br–C₆H₄–CO–CH₂–C₃H₇ | pyrrolidinyl-C₆H₄–CO–CH₂–C₃H₇ | 83–84.7 | calcd. 77.88 found 77.80 | 9.15 9.34 | 6.05 6.01 |
| 16 | azepane (N–H) | Br–C₆H₄–CO–CH₂–C₂H₅ | azepanyl-C₆H₄–CO–CH₂–C₂H₅ | 32–34 | calcd. 78.32 found 78.23 | 9.45 9.37 | 5.71 5.64 |
| 17 | azepane (N–H) | Br–C₆H₄–CO–CH₂–C₃H₇ | azepanyl-C₆H₄–CO–CH₂–C₃H₇ | 55.5–57.2 | calcd. 78.72 found 78.61 | 9.71 9.83 | 5.40 5.53 |
| 18 | morpholine (N–H) | Br–C₆H₄–CO–CH₂–C₄H₉ | morpholinyl-C₆H₄–CO–CH₂–C₄H₉ | 66–67 | calcd. 73.53 found 73.53 | 8.87 8.85 | 5.36 5.25 |
| 19 | morpholine (N–H) | Br–C₆H₄–CO–CH₂–C₅H₁₁ | morpholinyl-C₆H₄–CO–CH₂–C₅H₁₁ | 55–56 | calcd. 74.14 found 74.17 | 9.15 9.22 | 5.09 4.93 |
| 20 | morpholine (N–H) | Br–C₆H₄–CO–CH₂–C₆H₁₃ | morpholinyl-C₆H₄–CO–CH₂–C₆H₁₃ | 59–60 | calcd. 74.70 found 74.20 | 9.40 9.38 | 4.84 4.41 |
| 21 | morpholine (N–H) | Br–C₆H₄–CO–CH₂–CH(CH₃)–CH₂–C(CH₃)₃ | morpholinyl-C₆H₄–CO–CH₂–CH(CH₃)–CH₂–C(CH₃)₃ | 76–77.8 | calcd. 75.21 found 75.25 | 9.63 9.69 | 4.61 4.31 |

**% S: calculated: 12.86 found: 12.97

EXAMPLE 22

392.1 g (4.50 mol) of morpholine purum and 162.0 g (9.00 mol) of deionised water are placed in a 1 l high-pressure reactor. The reactor is closed and the solution is heated, with stirring, over about 1 hour to 220° C., the pressure in the reactor rising to 20 bar. Subsequently, 164.4 g (0.90 mol) of 1-(4-chlorophenyl)butan-1-one are uniformly added over 5 hours at 220° C. By the end of the addition, the pressure has fallen to about 18 bar and the reaction has run its course to more than 80%. The reaction mixture is then stirred for another five hours at 220° C., the pressure slowly falling to 17 bar. The reaction mixture is then allowed to cool to 80° C.

The morpholine salt is neutralised with 75.6 g (0.945 mol) of sodium hydroxide solution a 50%. A mixture of morpholine and water is then distilled off under reduced vacuum at 80° C. to 100° C. 180 g of deionised water and 203 g of special boiling-point spirit (110° C.–140° C. boling range) are then added. This mixture is clarified by filtration over a small amount of activated carbon at 80° C. The water phase is separated at 80° C. The product is crystallised out from the special boiling-point spirit, filtered and dried, giving the end product in a yield of 200.6 g 1-(4-morpholinophenyl)butan-1-one (c. 95.5% of theory). The beige product has a purity of >99.0% and a melting point of 64.80° C. Only product and educt are found in the filtrate.

Elemental analysis:

| | % C | | % H | | % N |
|---|---|---|---|---|---|
| calculated: | 72.07 | calculated: | 8.21 | calculated: | 6.00 |
| found: | 72.09 | found: | 8.26 | found: | 5.86 |

EXAMPLE 23

392.1 g (4.50 mol) of morpholine purum and 162.0 g (9.00 mol) of deionised water are placed in a 1 l high-pressure reactor. The reactor is closed and heated to 215° C. to 220° C. over about 60 minutes, the pressure reaching 19.9 bar. Subsequently, 164.4 g (0.90 mol) of 1-(4-chlorophenyl)butan-1-one in are added in liquid form using a pressure pump and the temperature is kept at 215° C.–220° C.

Duration of the addition: 3 hours. The pressure falls to 18.5 bar. Stirring is then continued for a further 3 hours at 215° C.–220° C., the pressure falling to 17.8 bar. The reaction solution is then cooled to about 80° C.

The reaction solution is transferred to a distillation apparatus and charged with 36.0 g (0.90 mol) of sodium hydroxide in pearl form. The water, and then also the morpholine, is removed by distillation at a temperature from 70° C. to 90° C. under reduced pressure. The final vacuum is about 30 mbar. The apparatus is released with nitrogen and then 171.8 g of deionised water and 30.2 g of toluene are added at about 88° C. After stirring, the water is separated off and the toluene is removed by distillation. The warm reaction solution is charged with 152.9 g of isopropanol and then clarified by filtration at about 65° C. over a pressure filter. The isopropanol solution is cooled and seeded. The suspension is filtered at about 0° C. and then washed with cold isopropanol, giving 186.7 g of 1-(4-morpholinophenyl)butan-1-one. (88.9% of theory) in the form of pale beige crystals having an m.p. of 64.4° C.–65.5° C.

EXAMPLE 24

164.4 g (0.90 mol) of 1-(4-chlorophenyl)butan-1-one, 392.1 g (4.50 mol) of morpholine purum, 162.0 g (9.00 mol) of deionised water and 0.89 g (0.90 mmol) of copper-I-chloride are placed in a 1 l high-pressure reactor. The reactor is closed and the solution is heated, with stirring, over about 1 hour to 180° C. The solution is then slowly heated further, raising the temperature by about 10° C. per hour. Over 4 hours, the solution reaches 220° C. and a pressure of 20 bar. The solution is allowed to react for another 5 hours at 220° C., the pressure slowly falling to 17 bar. The reaction solution is then allowed to cool to 80° C.

The morpholine salt is neutralised with 75.6 g (0.945 mol) of sodium hydroxide solution a 50% and the catalyst is precipitated. A mixture of morpholine and water is distilled off under reduced vacuum at 80° C.–100° C. Subsequently, 180 g of deionised water and 203 g of special boiling-point spirit (110° C.–140° C. boiling range) are added. The mixture is clarified by filtration over a small amount of activated carbon at 80° C. to remove the catalyst. The water phase is separated off at 80° C. The product is crystallised out from the special boiling-point spirit, filtered and dried, giving the end product in a yield of 199.8 g of 1-(4-morpholinophenyl)butan-1-one (c. 95.2% of theory). The beige product has a purity of >99.0% and a melting point of 64.8° C. Only product and educts are found in the filtrate.

EXAMPLE 25 a) 2-Bromo-1-(4-morpholinophenyl)butan-1-one

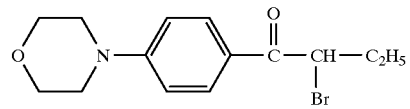

In a 2.5 l sulfonation flask, 466.6 g (2 mol) of 1-(4-morpholinophenyl)butan-1-one of Example 1 are dissolved in 600 ml (10.5 mol) of glacial acetic acid, the temperature falling to 5° C. With little cooling, 319.6 g (2 mol) of bromo are added dropwise to this mixture over about 2.5 hours at room temperature. The termination of the bromation is checked using a thin layer chromatogram. Subsequently, 300 g of ice are added to the reaction solution and then a sodium hydroxide solution, prepared from 1600 g (12 mol) of sodium hydroxide and 600 g of ice, is added dropwise over 1 hour, cooling well. The yellow suspension has a pH of approximately 6 and is then filtered and washed with water. The crystals are dried. They melt at a temperature of 99° C. to 102° C. The yield is 631.2 g of 2-bromo-1-(4-morpholinophenyl)butan-1-one. The $^1$H-NMR spectrum of the crude product corresponds to that of the indicated structure.

| Elemental analysis: | % C | % H | % N | % Br |
|---|---|---|---|---|
| calculated: | 53.86 | 5.81 | 4.49 | 25.59 |
| found: | 53.23 | 5.73 | 4.24 | 25.50 | b) 2-Dimethylamino-1-(4-morpholinophenyl)butan-1-one

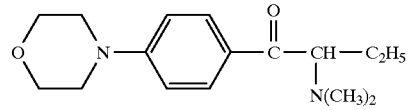

In a 2.5 l sulfonation flask, 312.2 g (1 mol) of 2-bromo-1-(4-morpholinophenyl)butan-1-one according to a) above are charged with 600 ml of methyl ethyl ketone and heated, with stirring, to 50° C. 207.3 g (1.5 mol) of potassium carbonate are added to the resulting solution and then 56.6 g (1.3 mol) of gaseous dimethylamine are run into the suspension over 1.5 hours at 50° C. The mixture is allowed to react for a further 4 to 5 hours until the thin layer chromatogram shows that there is no educt left. The suspension is then charged with 550 ml of water and stirred. The aqueous phase is separated and the 900 ml of organic phase, containing 2-dimethylamino-1-(4-morpholinophenyl)butan-1-one, is used in the next reaction step without any modification.

In a parallel test, the organic phase is concentrated. The crystals so obtained are recrystallised from hexane and dried, giving 235.1 g of pale yellow crystals which melt at a temperature from 53° C. to 56° C. The $^1$H-NMR spectrum of the product, 2-di-methylamino-1-(4-morpholinophenyl)butan-1-one, corresponds to the indicated structure.

| Elemental analysis: | % C | % H | % N |
|---|---|---|---|
| calculated: | 69.53 | 8.75 | 10.14 |
| found: | 68.91 | 8.59 | 9.74 | c) 2-Benzyl-2-dimethylamino-1-(4-morpholinophtenyl)butan-1-one

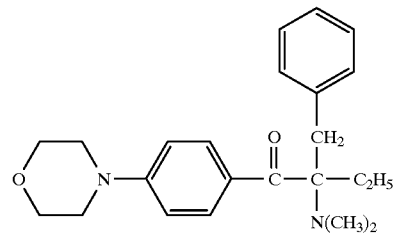

In a 2.5 l sulfonation flask, 900 ml of a solution (1 mol) of 2-dimethylamino-1-(4-morpholinophenyl)butan-1-one according to b) above are heated again to 50° C.179.7 g (1.05 mol) of benzyl bromide are then added dropwise over 20 minutes. The mixture is stirred for 3 to 4 hours at 50° C. until the thin layer chromatogram shows that there is no educt left. The temperature is raised to 60° C. and then 80 g (2 mol) of sodium hydroxide powder are added in increments over 45 minutes. The mixture is then stirred for another 1 to 2 hours at 50° C. until the thin layer chromatogram shows that there is no educt left. The reaction mixture is charged with 150 ml of water and stirred. The water phase is separated and the organic phase is concentrated on a vacuum rotary evaporator. 378.3 g of the yellowish crude product of 2-benzyl-2-dimethylamino-1-(4-morpholinophenyl)butan-1-one having a melting point from 102° C. to 110° C. remain in the flask. The crude product is dissolved hot in 600 ml of ethanol, cooled, crystallised, filtered and then washed with cold ethanol. The crystals are dried. They melt at 114° C. to 115° C., and gas chromatogram as well as thin layer chromatogram show them to be pure. The yield is 299.0 g of 2-benzyl-2-dimethylamino-1-(4-morpholinophenyl)butan-1-one. A further 22.4 g of pure product can be isolated from the mother liquor. The $^1$H-NMR spectrum of the pure product corresponds to that of the indicated structure.

| Elemental analysis: | % C | % H | % N |
|---|---|---|---|
| calculated: | 75.38 | 8.25 | 7.64 |
| found: | 75.23 | 8.21 | 7.58 |

What is claimed is:
1. A compound of formula (I)

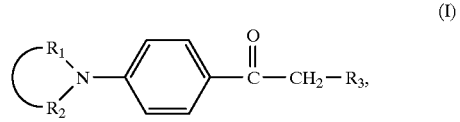

wherein:

$R_1$ and $R_2$ together are straight-chain or branched, unsubstituted or substituted $C_3$–$C_{20}$-alkylene optionally interrupted by one —$N(R_4)$ group, $R_3$ is straight-chain or branched, unsubstituted or substituted $C_2$–$C_{20}$alkyl, and $R_4$ is hydrogen, straight-chain or branched $C_1$–$C_3$alkyl, straight-chain or branched $C_3$–$C_5$-alkenyl, $C_7$–$C_9$-phenylalkyl, $C_1$–$C_4$-hydroxyalkyl or phenyl where, if $R_1$ and $R_2$ together are unsubstituted tetramethylene, $R_3$ is unsubstituted $C_6$alkyl.

2. A compound of formula I according to claim 1, wherein:

$R_1$ and $R_2$ together are $C_3$–$C_{20}$alkylene which is unsubstituted or substituted by hydroxy, $C_1$–$C_4$alkoxy, hydroxymethyl, $C_1$–$C_4$alkoxymethyl, —COO($C_1$–$C_4$alkyl) or phenyl $C_3$–$C_{20}$alkylene which is unsubstituted or substituted by hydroxy, $C_1$–$C_4$alkoxy group, $C_1$–$C_4$alkoxymethyl, —COO($C_1$–$C_4$alkyl) and which is optionally interrupted by one —$N(R_4)$ group, $R_3$ is $C_2$–$C_{20}$alkyl which is unsubstituted or substituted by $C_1$–$C_4$alkoxy, phenoxy, cyclohexyl or phenyl, and $R_4$ is hydrogen, $C_1$–$C_3$alkyl, $C_3$–$C_5$alkenyl, $C_7$–$C_9$phenylalkyl, $C_1$–$C_4$hydroxyalkyl or phenyl.

3. A compound of formula I according to claim 1, wherein:

$R_1$ and $R_2$ together are straight-chain or branched $C_4$–$C_{12}$alkylene optionally interrupted by a —$N(R_4)$ group, $R_3$ is $C_2$–$C_{10}$alkyl, and $R_4$ is hydrogen, $C_1$–$C_3$alkyl, allyl, benzyl or $C_2$–$C_3$hydroxyalkyl.

4. A compound of formula I according to claim 1, wherein:

$R_1$ and $R_2$, together with the linking N-atom, are a 6-membered ring which may additionally be interrupted by a —$N(R_4)$ group.

5. A compound of formula I according to claim 1, wherein:

$R_1$ and $R_2$ together are $C_4$–$C_6$alkylene optionally interrupted by a —$N(R_4)$ group, $R_3$ is straight-chain or branched, unsubstituted $C_2$–$C_7$alkyl, and $R_4$ is hydrogen or methyl.

6. A process for the preparation of a compound of formula I

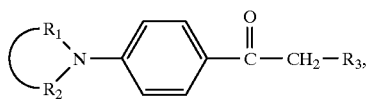

wherein
- $R_1$ and $R_2$ together are straight-chain or branched, unsubstituted or substituted $C_3$–$C_{20}$-alkylene optionally interrupted by one —$N(R_4)$ group,
- $R_3$ is straight-chain or branched, unsubstituted or substituted $C_2$–$C_{20}$alkyl, and
- $R_4$ is hydrogen, straight-chain or branched $C_1$–$C_3$alkyl, straight-chain or branched $C_3$–$C_5$-alkenyl, $C_7$–$C_9$phenylalkyl, $C_1$–$C_4$hydroxyalkyl or phenyl, by aminolysis of a p-halophenyl alkyl ketone of formula II

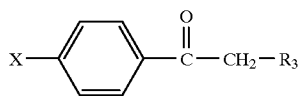

with a cyclic amine of formula III

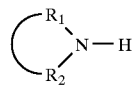

in water at a temperature of at least 130° C., in which formulae X is a halogen atom and $R_1$, $R_2$ and $R_3$ are as defined for formula I.

7. A process according to claim 6, which comprises using a p-halophenyl alkyl ketone of formula II, wherein X is chloro or bromo, and $R_3$ is as defined for formula I.

8. A process according to either claim 6 or claim 7, wherein the amount of cyclic amine of formula III is from about 2.5 to 12 molar equivalents, based on the p-halophenyl alkyl ketone of formula II.

9. A process according to any one of claims 6 to 8, wherein the amount of water is from about 1 to 100 molar equivalents, based on the p-halophenyl alkyl ketone of formula II.

10. A process according to any one of claims 6 to 9, which comprises carrying out the reaction under pressure in a pressure vessel.

11. A process according to any one of claims 6 to 10, wherein the temperature is in the range from about 140° C.–240° C.

12. A process according to any one of claims 6 to 11, which comprises placing the p-halophenyl alkyl ketone of formula II, together with the water and the cyclic amine, in a reaction vessel and heating it either immediately or slowly during the reaction until the final temperature is reached.

13. A process according to any one of claims 6 to 11, which comprises adding the p-halophenyl alkyl ketone of formula II during the reaction to the water and the cyclic amine which have been previously heated to the reaction temperature.

14. A process according to claim 6, which comprises placing 1 part of p-bromophenyl alkyl ketone or 1 part of p-chlorophenyl alkyl ketone of formula II, wherein $R_3$ is straight-chain or branched, unsubstituted $C_2$–$C_7$alkyl, with 5 parts of a cyclic amine of formula III, wherein $R_1$ and $R_2$ together are $C_4$–$C_6$alkylene optionally interrupted by a —$N(R_4)$ group and $R_4$ is hydrogen or methyl, and with 5 parts of water in a reaction vessel and reacting this mixture at a temperature from about 160° C.–180° C. in the case of p-bromo-phenyl alkyl ketone or from about 200° C.–230° C. in the case of p-chlorophenyl alkyl ketone.

15. A process according to claim 6, which comprises placing 10 to 20 parts of a cyclic amine of formula III, wherein $R_1$ and $R_2$ together are $C_4$–$C_6$alkylene optionally interrupted by a —$N(R_4)$ group and $R_4$ is hydrogen or methyl, with 20 to 40 parts of water in a reaction vessel, adding 2 to 4 parts of p-chlorophenyl alkyl ketone of formula II, wherein $R_3$ is straight-chain or branched, unsubstituted $C_2$–$C_7$alkyl, and reacting this mixture under pressure at about 210° C.–230° C.

* * * * *

UNITED STATES PATENT AND TRADEMARK OFFICE
CERTIFICATE OF CORRECTION

PATENT NO. : 5,977,357
DATED : NOVEMBER 2, 1999
INVENTOR(S) : RINALDO HÜSLER ET AL.

It is certified that error appears in the above-identified patent and that said Letters Patent is hereby corrected as shown below:

on the title page, Section [63] should read:

-- Related U.S. Application Data

[63] Divisional of application No. 08/847,519, April 21, 1997 --.

Signed and Sealed this

Fifth Day of September, 2000

Attest:

Q. TODD DICKINSON

*Attesting Officer*   *Director of Patents and Trademarks*